United States Patent
Shelchuk et al.

(10) Patent No.: US 6,882,887 B1
(45) Date of Patent: Apr. 19, 2005

(54) IMPLANTABLE LEAD AND ELECTRODE PORTION

(75) Inventors: Anne M. Shelchuk, San Rafael, CA (US); John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 219 days.

(21) Appl. No.: 10/321,307

(22) Filed: Dec. 16, 2002

(51) Int. Cl.[7] .................................. A61N 1/05
(52) U.S. Cl. .................................... 607/122
(58) Field of Search .................... 607/17, 99, 116, 607/119, 122, 123, 19

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,832,051 A * | 5/1989 | Jarvik et al. | 607/116 |
| 4,860,769 A * | 8/1989 | Fogarty et al. | 607/119 |
| 4,940,052 A | 7/1990 | Mann et al. | 128/419 PG |
| 5,366,493 A * | 11/1994 | Scheiner et al. | 607/116 |
| 5,466,254 A | 11/1995 | Helland | 607/123 |
| 5,476,483 A | 12/1995 | Bornzin et al. | 607/17 |
| 5,632,770 A * | 5/1997 | Schaldach | 607/122 |
| 6,011,995 A * | 1/2000 | Guglielmi et al. | 607/99 |

* cited by examiner

*Primary Examiner*—George Manuel

(57) ABSTRACT

An exemplary electrode portion, capable of placement in a vessel of a patient's body, includes a double helix. Exemplary implantable stimulation devices, lead assemblies and methods are also disclosed.

23 Claims, 9 Drawing Sheets

IMPLANTABLE LEAD AND ELECTRODE PORTION

TECHNICAL FIELD

The present invention generally relates to devices, systems and/or methods for providing cardiac pacing therapy. More particularly, various exemplary leads and/or electrode portions for implantation in a vessel are disclosed.

BACKGROUND

Most cardiac pacing therapies rely on transvenous implantation of one or more electrode-bearing leads for delivery of cardiac stimuli or for sensing cardiac activity. Such leads are often tubular in shape, as are their corresponding electrode portions. Such leads are typically inserted in a vein and then positioned to have the electrode portion in and/or near the heart. In general, if no mechanism is available to anchor the electrode portion, the position of the electrodes may change over time and thereby impair delivery of the intended therapy. Consequently, a variety of in vivo anchoring mechanisms have been developed. These mechanisms include tines, barbs, and even baskets. While such mechanisms have certain advantages, there are corresponding disadvantages. For example, barbs may be difficult to reposition once deployed, and baskets typically have a spherical shape that conforms well to only a single venous cross-section. Therefore, a need exists for new electrode-bearing leads and/or electrode portions. In particular, a need exists for electrode-bearing leads and/or electrode portions that can conform to a vessel's changing cross-section and that can be repositioned relatively easily, if necessary.

SUMMARY

An exemplary electrode portion, capable of placement in a vessel of a patient's body, includes a double helix. Exemplary implantable stimulation devices, lead assemblies and methods are also disclosed.

The various apparatus and methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims.

Exemplary Stimulation Device

The techniques described below are intended to be implemented in connection with any stimulation device that is configured or configurable to stimulate or shock a patient's heart.

Figure 1:
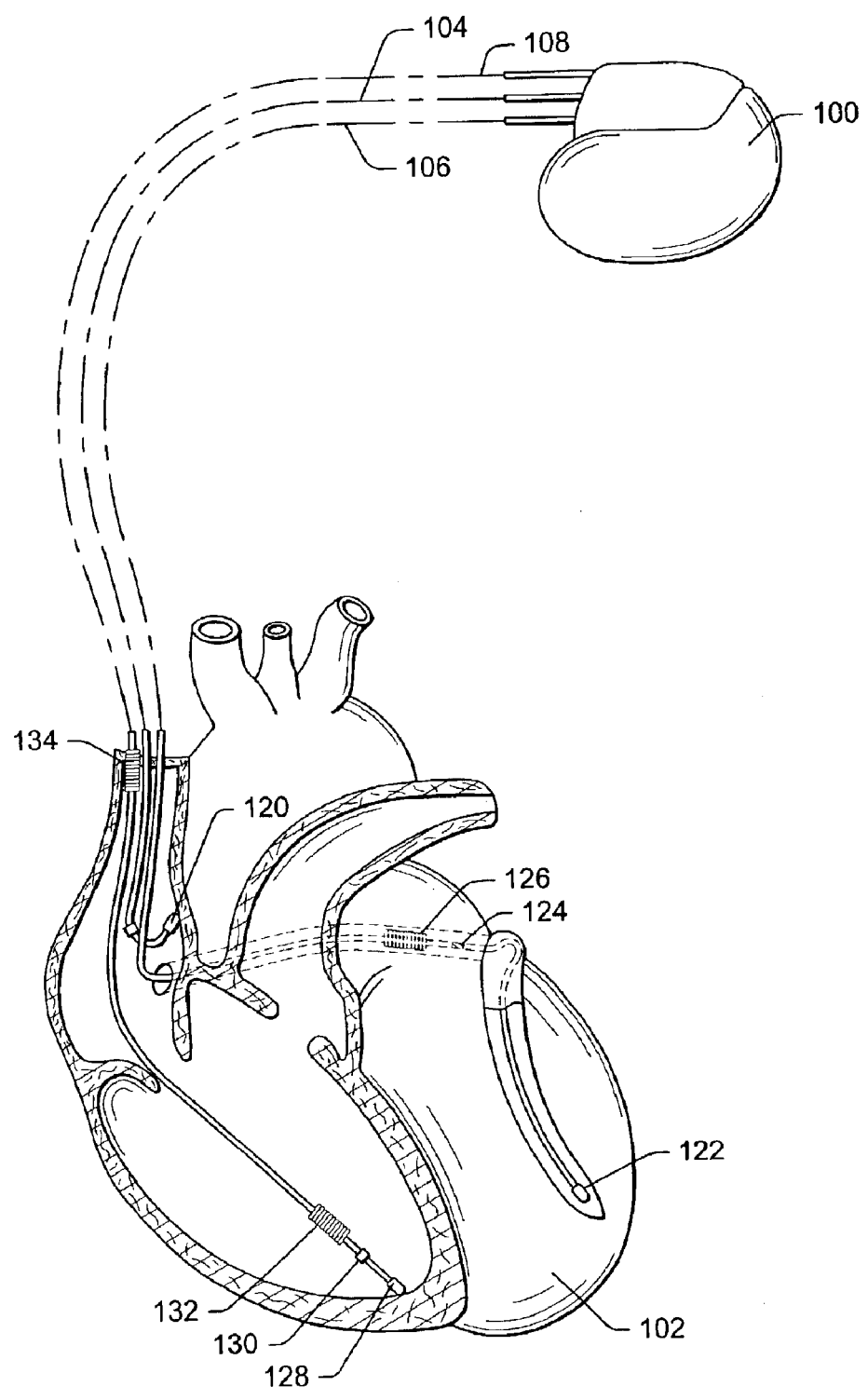
FIG. 1 is a simplified diagram illustrating an implantable stimulation device in electrical communication with at least three leads implanted into a patient's heart for delivering multi-chamber stimulation and shock therapy.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage or septum.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132, and superior vena cava (SVC) coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Figure 2:
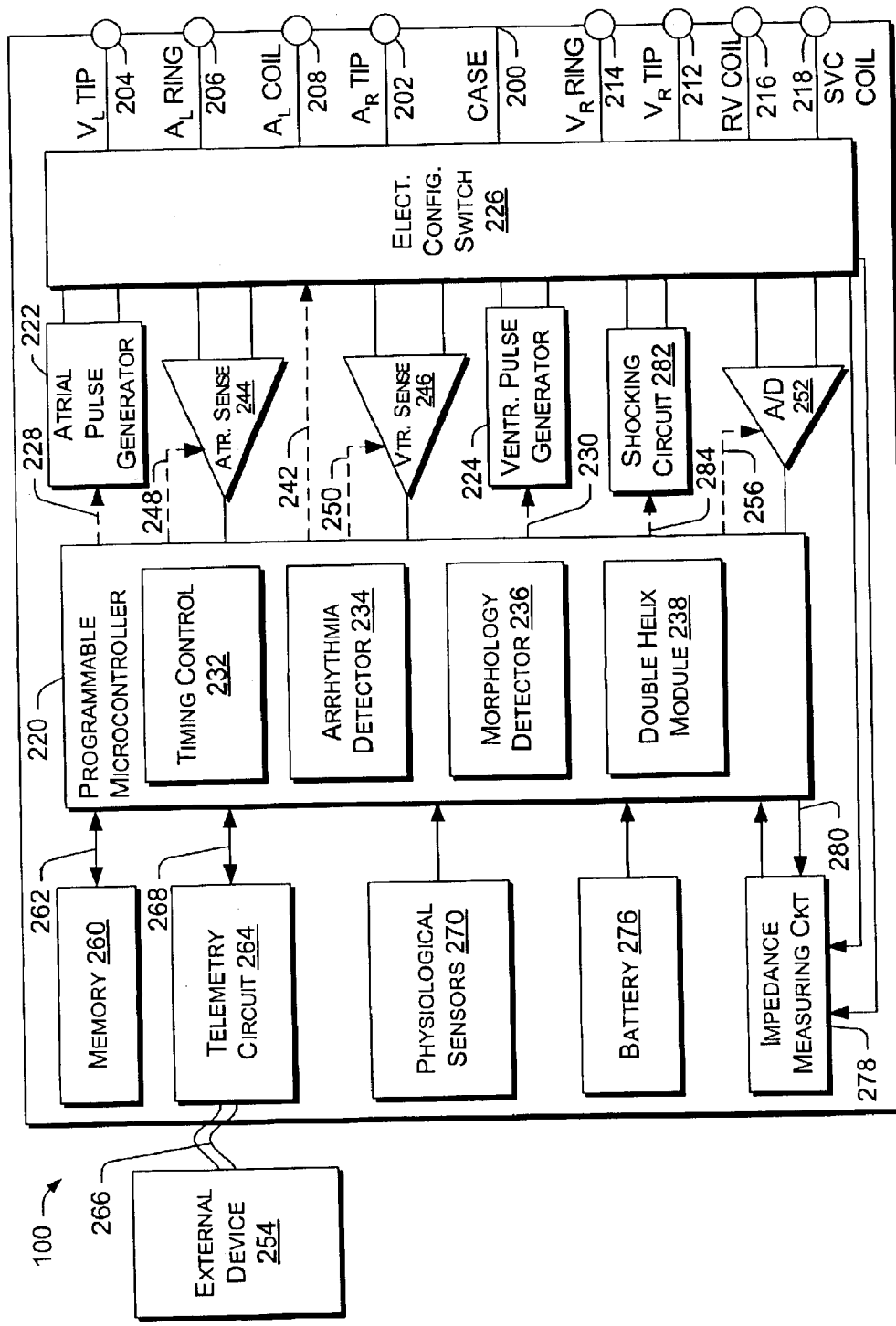
FIG. 2 is a functional block diagram of a multi-chamber implantable stimulation device illustrating basic elements that are configured to provide cardioversion, defibrillation, and pacing stimulation to the heart and/or other tissues stimulation in various places in a patient's body.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein.

For a more detailed description of the various timing intervals used within the stimulation device and their interrelationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrioventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 optionally includes a double-helix module 238 for performing a variety of tasks related to use of an exemplary double-helix electrode portion, as described in more detail below. This component can be utilized by the stimulation device 100 for aiding in implantation or positioning, electrode selection (configuration, polarity, etc.), and administration of various therapies, including tissue stimulation to effect the myocardium and/or other tissue and/or nerves. The double-helix module 238 may be implemented in hardware as part of the microcontroller 220, or as software/firmware instructions programmed into the device and executed on the microcontroller 220 during certain modes of operation. Of course, such an exemplary electrode portion and/or module 238 may be optionally used for sensing. In general, such a module typically includes software and/or hardware for selectively delivering power to one or more electrodes of a double helix electrode portion.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise (or physiological) state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, oxygen saturation, ventricular gradient, and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et. al), issued Dec. 19, 1995, which patent is hereby incorporated by reference.

More specifically, the physiological sensors 270 optionally include sensors to help detect movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. The device 100 optionally employs lithium battery chemistry or other suitable power technology.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic implant phases for proper lead functioning, positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3:
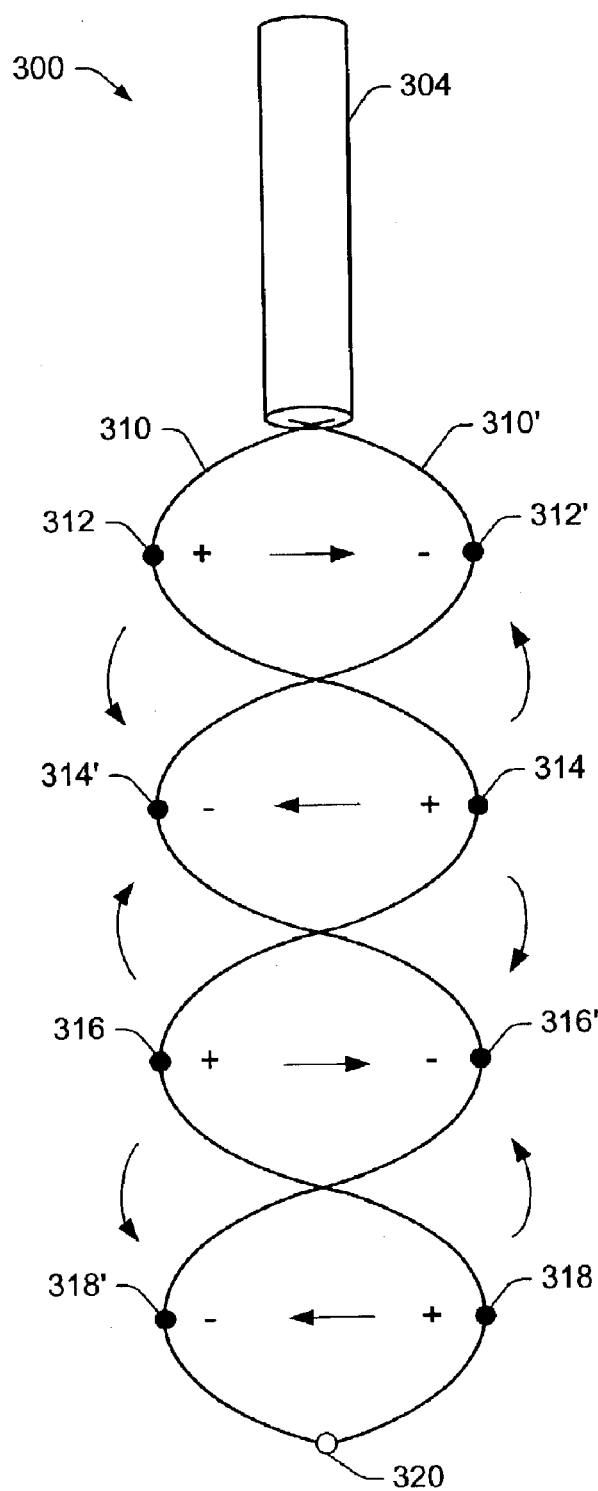
FIG. 3 is a side-view of an exemplary double-helix electrode portion.

Referring to FIG. 3, an exemplary electrode portion 300 is shown. The electrode portion 300 is suitable for use with devices such as the exemplary device 100 described with reference to FIGS. 1 and 2, for example, a lead connected to the device 100 may include such an electrode portion. As shown in FIG. 3, the electrode portion 300 includes a first conductor 310 and a second conductor 310' which form a double-helix. In this example, the two conductors 310, 310' join at a joiner 320 positioned at a distal end. The joiner 320 optionally includes an insulator for electrically insulating the first conductor 310 from the second conductor 310'. Alternatively, the first conductor 310 and the second conductor 310' form part of a conduction circuit suitable for use in unipolar stimulation. For purposes of illustration, the electrode portion 300 includes a lead end 304 that houses at least part of the conductors 310, 310' or to which the conductors 310, 310' are attached. In the former instance, the conductors 310, 310' are extendable and/or retractable from the lead end 304.

As shown in FIG. 3, each conductor 310, 310' has one or more electrodes. In this particular example, the conductor 310 includes four electrodes 312, 314, 316, 318, labeled "+", whereas the conductor 310' includes four electrodes 312', 314', 316', 318' labeled "−". In general, the conductors 310, 310' have an insulated coat or coating between electrodes. A variety of arrows indicate possible bipolar conduction routes from each "+" electrode to one or more "−" electrodes. Thus, when the electrode portion 300 is implanted in a patient's body and used to carry a stimulation pulse, a variety of conduction paths are available. Note that in this particular configuration, each positive electrode (e.g., the electrode 316) has three neighboring negative, electrodes (e.g., the electrodes 314', 316', 318'). According to this example, at least one of the electrodes of one of the conductors has three nearest neighbor electrodes associated with the other conductor. Of course, other configurations are possible wherein electrodes are placed at other positions along one or both of the conductors. Further, such an exemplary electrode portion optionally includes a third conductor, for example, a central conductor which travels along the axis of a double-helix configuration. In this example, the two double-helix conductors optionally have the same polarity and the central conductor has a different polarity. Yet further, the electrodes of a first conductor and/or a second conductor are optionally formed by gaps in an insulator coat or coating of the first conductor and/or the second conductor, respectively. In addition, a unipolar configuration optionally uses a distant object, such as a stimulation device can, as an electrode.

Figure 4:
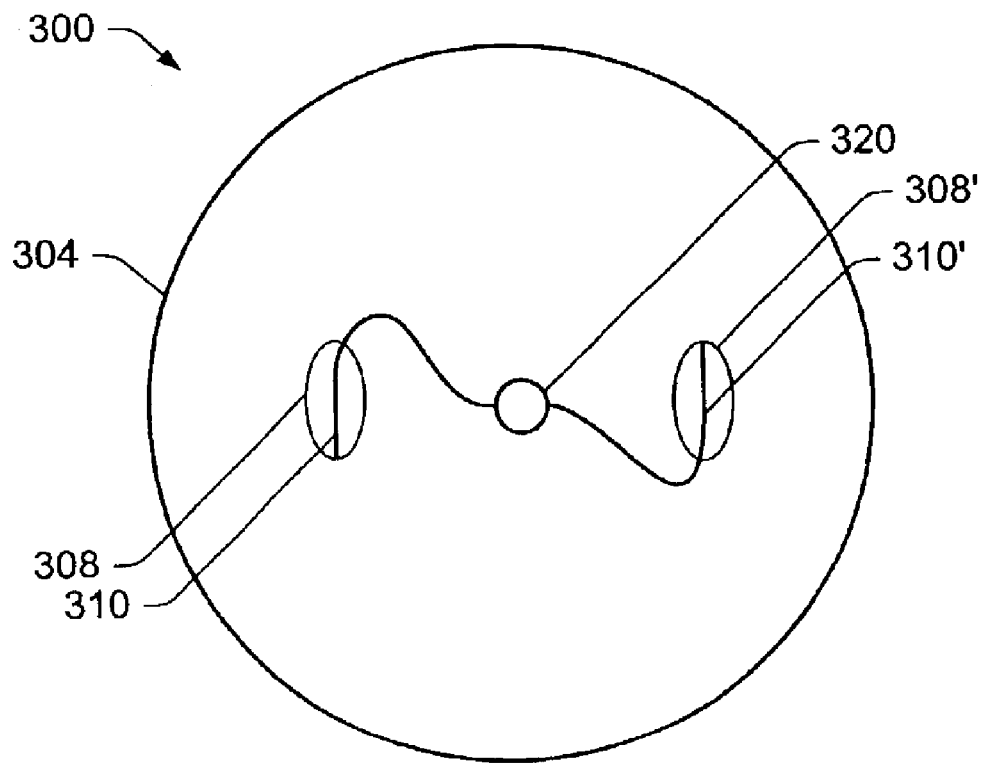
FIG. 4 is a front-end view of an exemplary double-helix electrode portion.

Referring to FIG. 4, a front view of an exemplary electrode portion 300 is shown. The electrode portion 300 includes a lead end 304 having two apertures 308, 308'. A first conductor 310 is positioned in the one aperture 308 while a second conductor 310' is positioned in the other aperture 308'. The two conductors 310, 310' join at a joiner 320. In this particular example, the two conductors 310, 310' form a double-helix electrode portion when extended from the lead end 304. An exemplary method of positioning a double-helix electrode portion involves positioning a lead in a vessel, wherein the lead has a lead end such as the lead end 304, and then extending the double-helix electrode portion into the vessel or a joining vessel once the lead has been positioned.

Figure 5:
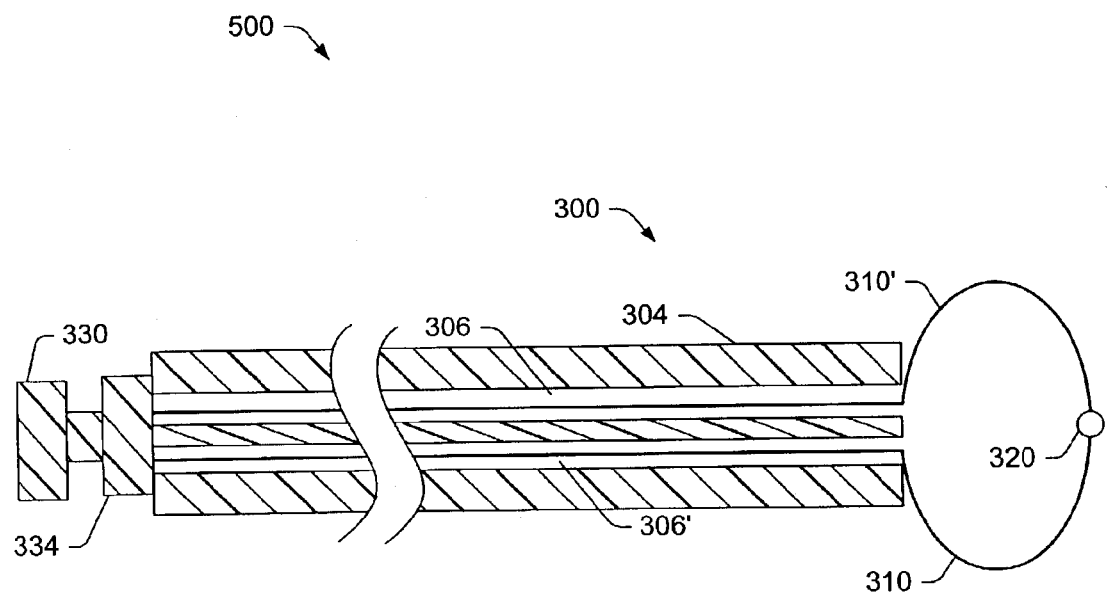
FIG. 5 is a cross-sectional view of an exemplary lead and electrode portion.

Referring to FIG. 5, a cross-sectional view of an exemplary lead assembly 500 is shown. The lead assembly 500 includes an exemplary electrode portion 300 having a lead end 304 and two conductors 310, 310' capable of extending from the lead end 304 to form a double-helix electrode portion. The two conductors 310, 310' join at an insulator 320 positioned at the distal end of the electrode portion 300.

At the lead end 304, the conductors 310, 310' are positioned in two channels 306, 306' that travel approximately the length of the lead assembly 500 and terminate at a proximal lead assembly end 334 to which a plunger 330 is fitted to aid in extension and/or retraction of the conductors 310, 310'. Of course, a variety of other mechanisms for extension and/or retraction are possible (e.g., screw or auger mechanisms, simple piston, etc.). In addition, the channels 306, 306' end at apertures such as the apertures 308, 308' shown in the exemplary lead end 304 of FIG. 4.

In this exemplary lead assembly 500, the two conductors 310, 310' are optionally constructed from a flexible shape-memory material having a memory for a double-helix. Some examples of shape-memory alloys include copper-zinc-aluminum, iron-manganese-silicon, gold-cadmium, copper-aluminum, copper-aluminum-nickel, and nickel-titanium. The memory material may be a conductor material and/or an insulator material for housing a flexible conductor capable of conforming to the memory shape of the insulator. In this example, the conductors 310, 310' have sufficient flexibility to allow for travel in the channels 306, 306'. Alternatively, both conductors 310, 310' travel in a single channel of a lead. In this example, at least one of the conductors 310, 310' has an insulator coat or coating.

Figure 6:
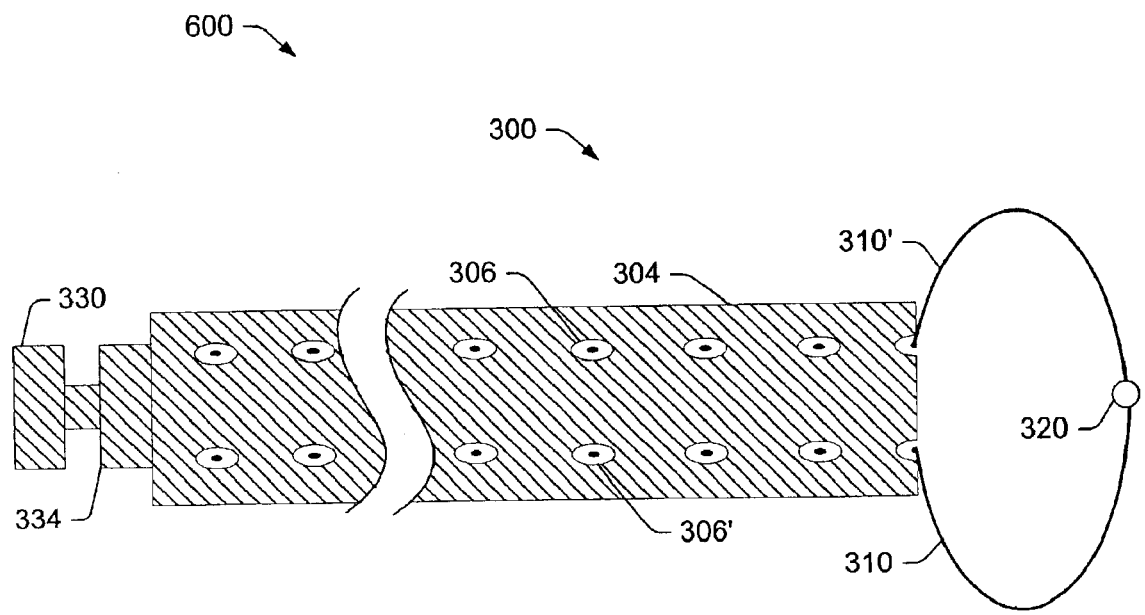
FIG. 6 is a cross-sectional view of another exemplary lead and electrode portion.

Referring to FIG. 6, a cross-sectional view of another exemplary lead assembly 600 is shown. The lead assembly 600 includes an exemplary electrode portion 300 having a lead end 304 and two conductors 310, 310' capable of extending from the lead end 304 to form a double-helix electrode portion. The two conductors 310, 310' join at an insulator 320 positioned at the distal end of the electrode portion 300. At the lead end 304, the conductors 310, 310' are positioned in two helical channels 306, 306' that travel approximately the length of the lead assembly 600 and terminate at a proximal lead assembly end 334 to which a plunger 330 is fitted to aid in extension and/or retraction of the conductors 310, 310'. Of course, a variety of other mechanisms for extension and/or retraction are possible (e.g., screw or auger mechanisms, simple piston, etc.). In addition, the helical channels 306, 306' end at apertures such as the apertures 308, 308' shown in the exemplary lead end 304 of FIG. 4. When extended from the lead end 304, the maximum radial dimension of the double-helix, formed by conductors 310, 310', is typically larger than that of the lead end 304.

In this exemplary lead assembly 600, the two conductors 310, 310' are optionally constructed from a flexible shape-memory material having a memory for a double-helix. The memory material may be a conductor material and/or an insulator material for housing a flexible conductor capable of conforming to the memory shape of the insulator. In this example, the conductors 310, 310' have sufficient flexibility to allow for travel in the channels 306, 306'. Alternatively, the conductors 310, 310' have a preformed helical shape or a helical shape, in part, dictated by the helical channels 306, 306'.

Figure 7:
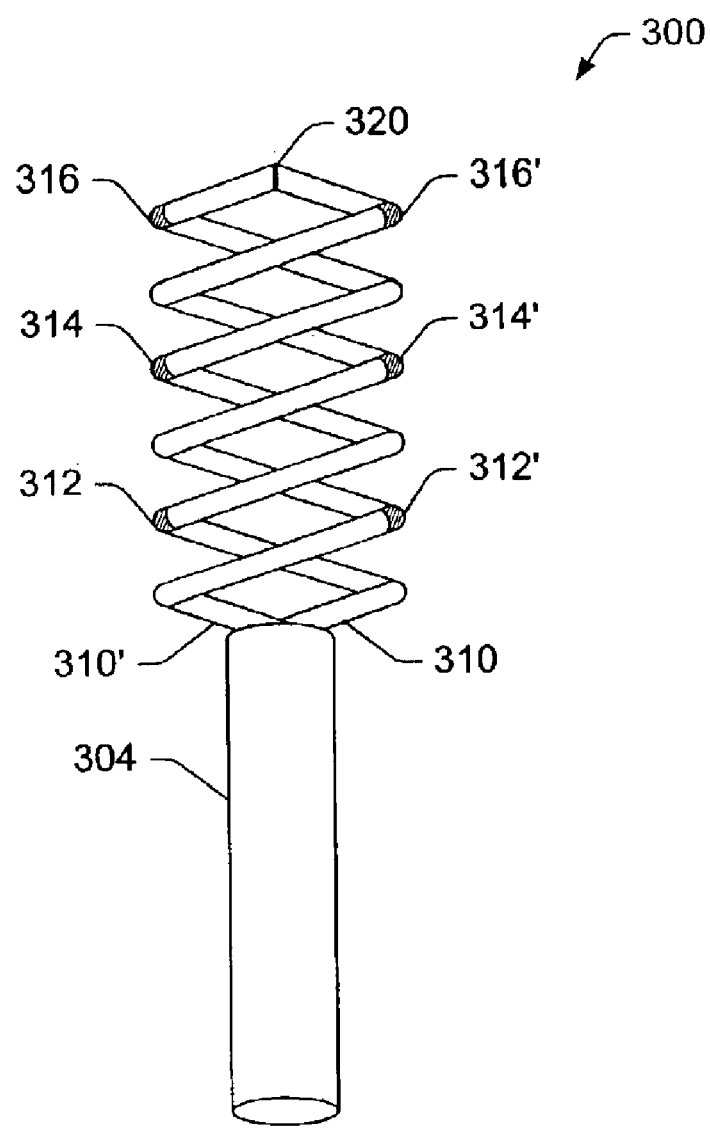
FIG. 7 is a side-view of an exemplary double-helix electrode portion.

Referring to FIG. 7, another exemplary electrode portion 300 is shown. The electrode portion 300 includes a lead end 304 and two conductors 310, 310' which form a double-helix. Each conductor 310, 310' includes a plurality of electrodes. For example, the conductor 310 has three electrodes 312, 314, 316 whereas the conductor 310' has three electrodes 312', 314', 316'. Further, an insulator and/or joiner 320 joins and/or insulates the two conductors 310, 310'. In this particular example, the double-helix has a diameter larger than that of the lead end 304. Of course, other examples may have a double-helix with a diameter smaller, larger, and/or equal to the diameter or other characteristic dimension (e.g., width) of a lead. Where it is desirable to anchor or secure the electrodes in a vessel, the use of a diameter large enough to bias at least part of the electrode portion against a vessel wall may aid in anchoring and/or securing one or more of the electrodes.

Figure 8:
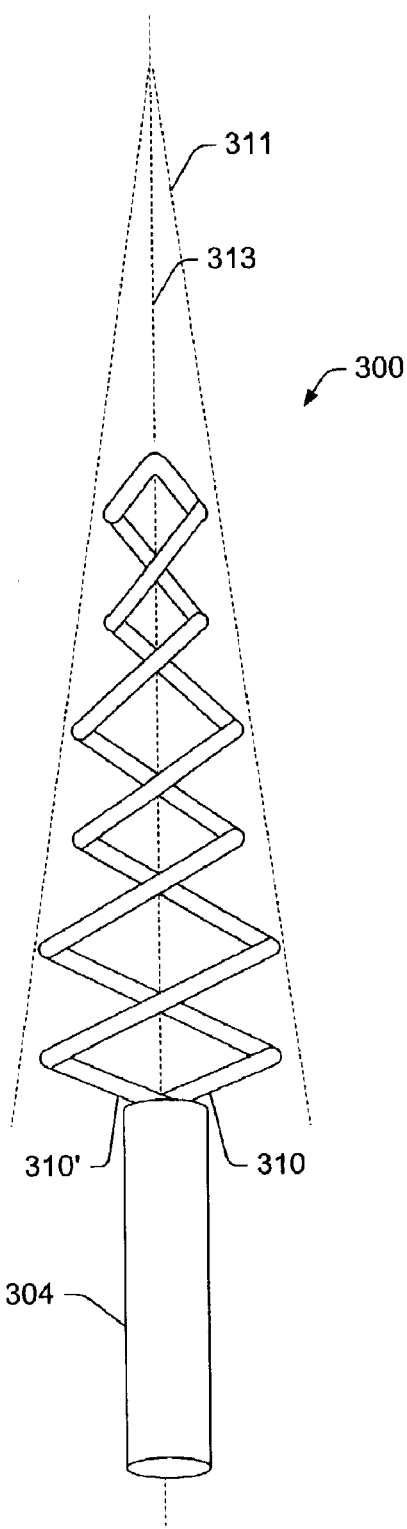
FIG. 8 is a side-view of an exemplary tapered double-helix electrode portion.

Referring to FIG. 8, yet another exemplary electrode portion 300 is shown. The electrode portion 300 includes a lead end 304 and two conductors 310, 310'. In this example, the conductors 310, 310' form a tapered double-helix having an approximate taper angle 311 wherein the distal diameter of the double helix is less than the proximal diameter. As shown in FIG. 8, the taper angle 311 is defined from a central axis 313. This particular exemplary electrode portion is suitable for positioning in tapered vessels. Further, use of a taper may aid in anchoring and/or securing one or more of the electrodes.

Figure 9:
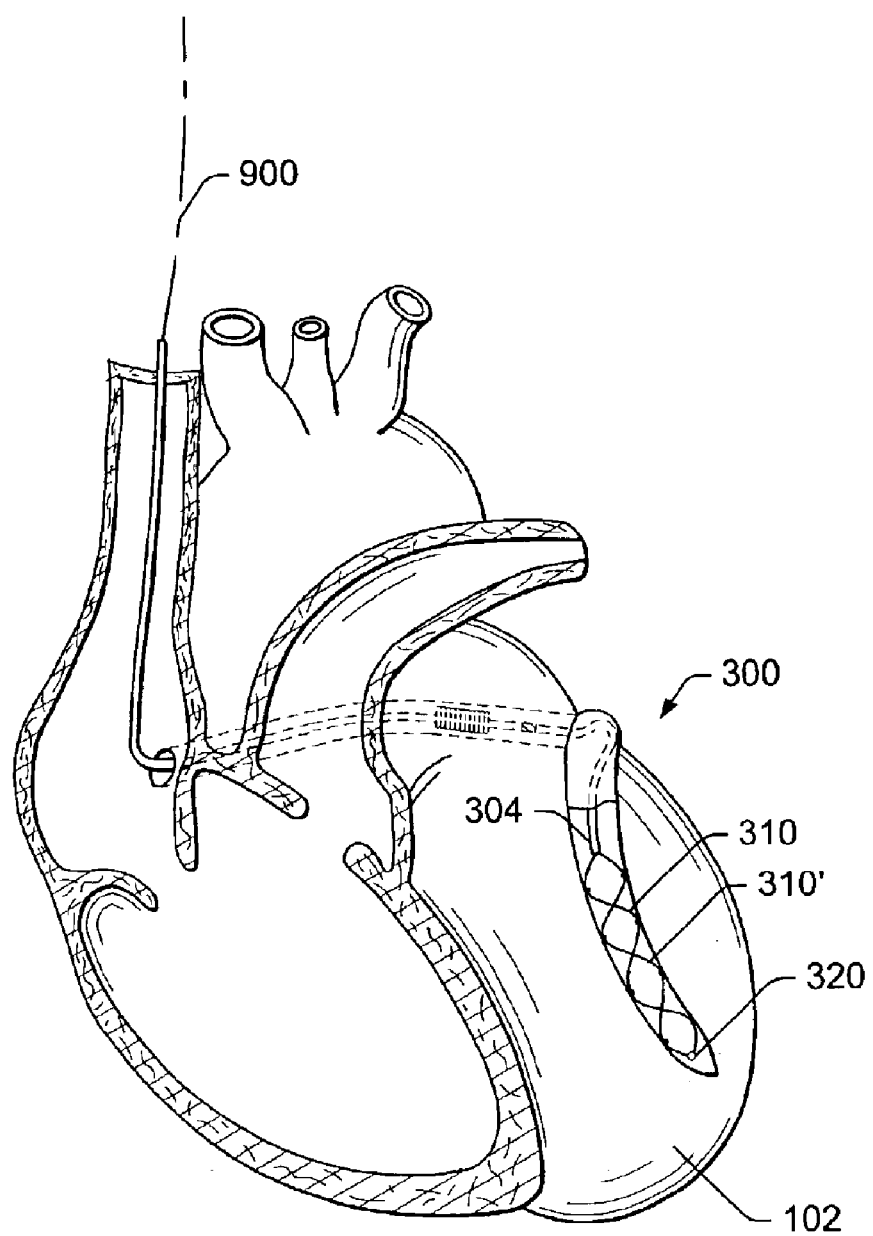
FIG. 9 is an approximate anatomical view of an exemplary implanted double-helix electrode portion.

Referring to FIG. 9, an exemplary lead 900 is shown positioned in a vessel of a heart 102. The lead 900 optionally attaches to an implantable stimulation device, such as, but not limited to, the device 100 of FIGS. 1 and 2. The lead 900 includes an exemplary double-helix electrode portion 300 attached to a lead end 304. The electrode portion 300 includes two conductors 310, 310' which form a double-helix and join at an insulator 320. In this example, the electrode portion 300 is suitable for use in stimulation of the myocardium and/or autonomic nerves. Note that the configuration of the exemplary electrode portion 300 may also aid in anchoring and/or otherwise securing the electrodes.

CONCLUSION

Although various exemplary devices and/or methods have been described in language specific to structural features and/or methodological acts, it is to be understood that the subject matter defined in the appended claims is not necessarily limited to the specific features or acts described. Rather, the specific features and acts are disclosed as exemplary forms of implementing the claimed subject matter.

What is claimed is:

1. An implantable lead to provide cardiac stimulation pulses to a patient's heart, the implantable lead comprising:
    a lead body having a proximal portion and a distal portion, the proximal portion coupled to an implantable cardiac stimulation device; and
    an electrode portion disposed at the distal portion, the electrode portion comprising:
        a lead end, the lead end being a distal end of the lead body;
        a first conductor having one or more pacing electrodes positioned distally from the lead end;
        a second conductor having one or more pacing electrodes positioned distally from the lead end;
        wherein the first conductor and the second conductor form a double helix.

2. The electrode portion of claim 1, further comprising a joiner for joining a distal end of the first conductor to a distal end of the second conductor.

3. The electrode portion of claim 2, wherein the joiner comprises an insulator for electrically insulating the first conductor from the second conductor.

4. The electrode portion of claim 1, wherein the double helix tapers from a proximal end to a distal end.

5. The electrode portion of claim 1, wherein the first conductor and/or the second conductor comprise a shape-memory material.

6. The electrode portion of claim 1, wherein the first conductor and/or the second conductor have an insulator coat or coating.

7. The electrode portion of claim 6, wherein gaps in the insulator coat or coating form the one or more electrodes of the first conductor and/or the one or more electrodes of the second conductor.

8. The electrode portion of claim 1, wherein the lead body comprises a first channel for the first conductor and a second channel for the second conductor.

9. The electrode portion of claim 1, wherein the lead body comprises a channel for the first conductor and the second conductor.

10. The electrode portion of claim 1, wherein the first conductor and the second conductor are extendable from the lead body, and wherein the double helix is distal to the lead end when extended.

11. The electrode portion of claim 1, further comprising one or more connector terminals for connecting the first conductor and/or the second conductor to the implantable cardiac stimulation device.

12. The electrode portion of claim 11, wherein the implantable cardiac stimulation device includes software and/or hardware for selectively delivering power to one or more electrodes of the electrode portion.

13. The electrode portion of claim 1, wherein at least one of the electrodes of one of the conductors has three nearest neighbor electrodes associated with the other conductor.

14. The electrode portion of claim 1, further comprising a unipolar configuration.

15. The electrode portion of claim 1, further comprising a bipolar configuration.

16. A method to stimulate a patient's heart, comprising:
providing a lead to be coupled to an implantable cardiac stimulation device, the lead having a lead body with a proximal portion and a distal portion;
positioning the distal portion of the lead body in a vessel of a patient's body;
providing an electrode portion having pacing electrodes, the electrode portion moveable from a retracted position to and extended position, the lead body housing the electrode portion when in the retracted position, and the electrode portion extending distally outwardly from the distal portion of the lead body when in the extended position; and
distally extending the electrode portion from a distal end of the distal portion wherein the electrode portion comprises a double helix.

17. The method of claim 16, further comprising delivering power to the electrode portion.

18. The method of claim 16, wherein the electrode portion comprises two conductors.

19. The method of claim 16, wherein the electrode portion comprises a shape-memory material.

20. The method of claim 16, wherein the double helix biases a vessel.

21. An implantable cardiac lead for implant in the coronary sinus of the heart and for use with an implantable cardiac stimulation device for pacing the left heart, the lead comprising:
a lead body having a proximal portion and a distal portion; and
a double helix electrode portion disposed at a distal end of the distal portion, the double helix electrode portion comprising:
a first conductor having one or more pacing electrodes and a second conductor having one or more pacing electrodes; and
an electrically insulative joiner to join a distal end of the first conductor to a distal end of the second conductor.

22. The lead of claim 21, wherein the double helix electrode portion is moveable from a retracted position to an extended position, wherein the double helix electrode portion is housed within the lead body when in the retracted position, and wherein the double helix electrode portion is extended distally from the distal end of the lead body when in the extended position.

23. The lead of claim 21, wherein the double helix electrode portion tapers from a proximal end to a distal end.

* * * * *